US005554665A

United States Patent [19]
Tateosian et al.

[11] Patent Number: 5,554,665
[45] Date of Patent: Sep. 10, 1996

[54] METHOD AND DISPENSER FOR MAKING DENTAL PRODUCTS

[75] Inventors: Louis H. Tateosian, York; Scott E. Shaffer, Jacobus; Mark A. Latta, York, all of Pa.

[73] Assignee: Dentsply Research & Development Corp., Milford, Del.

[21] Appl. No.: 430,705

[22] Filed: Apr. 28, 1995

Related U.S. Application Data

[63] Continuation of Ser. No. 81,940, Jun. 23, 1993, abandoned.

[51] Int. Cl.$^6$ ........................................................... C08F 2/46
[52] U.S. Cl. ........................ 522/30; 522/24; 522/48; 522/908; 433/90; 264/17; 264/18
[58] Field of Search ........................ 522/30, 48, 908, 522/24; 433/90; 264/17, 18

[56] References Cited

U.S. PATENT DOCUMENTS

| | | |
|---|---|---|
| 3,435,012 | 3/1969 | Nordlander . |
| 3,661,876 | 5/1972 | Wegemund et al. . |
| 3,899,382 | 8/1975 | Matsuda et al. . |
| 3,969,303 | 7/1976 | Prosen ............................. 260/31.8 C |
| 4,129,611 | 12/1978 | Heiss . |
| 4,267,133 | 5/1981 | Kohmura et al. . |
| 4,331,580 | 5/1982 | Bunyan . |
| 4,337,349 | 6/1982 | Orlowski et al. ........................ 560/30 |
| 4,431,787 | 2/1984 | Werber . |
| 4,538,920 | 9/1985 | Drake ............................. 366/177 |
| 4,602,076 | 7/1986 | Ratcliffe et al. . |
| 4,657,941 | 4/1987 | Blackwell et al. . |
| 4,674,980 | 6/1987 | Ibsen et al. . |
| 4,771,112 | 9/1988 | Engelbrecht . |
| 4,806,381 | 2/1989 | Engelbredcht et al. . |
| 4,816,495 | 3/1989 | Blackwell et al. . |
| 4,842,936 | 6/1989 | Kashihara et al. . |
| 4,872,936 | 10/1989 | Engelbrecht . |
| 4,880,857 | 11/1989 | Mori et al. . |
| 4,940,749 | 7/1990 | Mori et al. . |
| 4,994,520 | 2/1991 | Mori et al. . |
| 5,033,650 | 7/1991 | Colin ............................. 222/137 |
| 5,037,473 | 8/1991 | Antonucci et al. . |
| 5,091,441 | 2/1992 | Omura . |
| 5,183,834 | 2/1993 | Gorlich et al. ............................. 523/105 |
| 5,218,070 | 6/1993 | Blackwell . |

FOREIGN PATENT DOCUMENTS

| | | |
|---|---|---|
| 1145880 | 5/1980 | Canada . |
| 1102039 | 5/1981 | Canada . |
| 1148294 | 6/1983 | Canada . |
| 1149538 | 7/1983 | Canada . |
| 1189996 | 7/1985 | Canada . |
| 1200046 | 1/1986 | Canada . |
| 1209298 | 8/1986 | Canada . |
| 1243796 | 10/1988 | Canada . |
| 1245437 | 11/1988 | Canada . |
| 1244581 | 11/1988 | Canada . |
| 1244177 | 11/1988 | Canada . |
| 1259149 | 9/1989 | Canada . |
| 2002017 | 11/1989 | Canada . |
| 1262791 | 11/1989 | Canada . |
| 2009471 | 2/1990 | Canada . |
| 2032773 | 6/1991 | Canada . |
| 2033405 | 7/1991 | Canada . |
| 2051333 | 3/1992 | Canada . |
| 185431 | 12/1984 | European Pat. Off. . |
| 0319639 | 6/1989 | European Pat. Off. . |
| 0334256 | 9/1989 | European Pat. Off. . |
| 2189793 | 11/1987 | United Kingdom . |
| WO87/05800 | 10/1987 | WIPO . |

OTHER PUBLICATIONS

*In Vitro Properties of Light–Polymerized Reline materials*, by Smith, Powers, vol. 4 No. 5 (1991) pp. 455–458.

The International Journal of Prosthodontics.

Bosworth Lightliner Hard, Astron Light Cure Hard Reline.

A comparison of monomer conversion and inorganic filler content in visible light–cured denture resins, by Barron, Rueggeberg, and Schuster, Dent Mater 8:274–277, Jul. 1992.

Dentsply's Reprosil Cartridge System, Instructions.

Caulk's Hydrosil XT, Instructions.

Accelerated degradation testing, by O'Fagain, Sheehan, and O'Kennedy, *American Biotechnology Laboratory* vol. 9, No. 9, pp. 31–32, Oct. 1991.

*Primary Examiner*—Mark Chapman
*Attorney, Agent, or Firm*—Dale R. Lovercheck; James B. Bieber

[57] ABSTRACT

A method of forming dental products, such as dentures, denture relines, dental crowns, dental bridges and dental restorative materials, temporary crown, temporary bridge, provisional crown or provisional bridge, from two polymerizable paste compositions each having a complimentary component of a free radical catalyst system and a polymerizable acrylic compound. One of these paste compositions includes an oxidizing agent and a stabilizer and the other includes a reducing agent as components of a redox catalyst system for free radical polymerization. These paste compositions are mixed in a static mixer to form a polymerizing paste composition, which is then shaped into a dental prosthesis. A handheld mixing dispenser useful in carrying out this method, includes a static mixing conduit, and two containers enclosing the polymerizable paste compositions. The static mixing conduit encloses a static mixing member. The containers are adapted to be connected in fluid flow communication with the static mixing conduit. In the paste composition which includes the reducing agent a photoinitiator may be preferably included. Each container is sufficiently oxygen permeable to maintain inhibition of polymerization of the polymerizable paste composition therein for at least 12 months at 23° C.

21 Claims, 4 Drawing Sheets

METHOD AND DISPENSER FOR MAKING DENTAL PRODUCTS

This is a continuation of application Ser. No. 08/081,940, filed Jun. 23, 1993 now abandoned.

The invention relates to packaging, storing, mixing and applying paste compositions useful in forming prosthetic products. The invention provides free radical polymerizable acrylic paste compositions enclosed in an air permeable container connected to a static mixing channel, which are useful to form dental products such as dental appliances and dental prostheses, for example dentures, denture relines, dental crowns, dental bridges and dental restorative materials.

Birger in U.S. Pat. No. 3,435,012 discloses anaerobic sealant composition containing monoacrylate esters. Bernd et al in U.S. Pat. No. 3,661,876 discloses adhesives or sealing agents which harden on exclusion of oxygen. Matsuda et al in U.S. Pat. No. 3,899,382 discloses anaerobic bonding agent. Heiss in U.S. Pat. No. 4,129,611 discloses thermoplastic polyurethanes of mixtures of hard and soft thermoplastic polymers. Kohmura et al in U.S. Pat. No. 4,267,133 discloses manufacture of denture base. Bunyan in U.S. Pat. No. 4,331,580 discloses flowable anaerobic sealant composition. Werber in U.S. Pat. No. 4,431,787 discloses anaerobic adhesives. Ratcliffe et al in U.S. Pat. No. 4,602,076 discloses photopolymerizable compositions. Blackwell et al in U.S. Pat. No. 4,657,941 discloses biologically compatible adhesive containing a phosphorus adhesion promoter and a sulfinic accelerator. Ibsen et al in U.S. Pat. No. 4,674,980 discloses dental composite and porcelain repair. Engelbrecht in U.S. Pat. No. 4,771,112 discloses compounds that consist of aldehyde, epoxide isocyanate, or halotriazine groups of polymerizable groups, and of a higher-molecular backbone, mixtures that contain them, and the use thereof. Engelbrecht et al in U.S. Pat. No. 4,806,381 discloses polymerizable compounds containing acid and acid derivatives, mixtures containing the same, and use thereof. Blackwell et al in U.S. Pat. No. 4,816,495 discloses biologically compatible adhesive visible light curable compositions. Kashihara et al in U.S. Pat. No. 4,842,936 discloses composite basic resin particles, its preparation and resinous composition for coating use containing the same. Engelbrecht in U.S. Pat. No. 4,872,936 discloses polymerizable cement mixtures. Mori et al in U.S. Pat. No. 4,880,857 discloses carbon black-graft polymer, method for production thereof, and use thereof. Mori et al in U.S. Pat. No. 4,940,749 discloses carbon black-graft polymer method for production thereof, and use thereof. Mori et al in U.S. Pat. No. 4,994,520 discloses carbon black-graft polymer, method for production thereof, and use thereof. Antonucci et al in U.S. Pat. No. 5,037,473 discloses denture liners. Omura in U.S. Pat. No. 5,091,441 discloses dental composition. Blackwell in U.S. Pat. No. 5,218,070 discloses dental/medical compositions and use. Ying in Canadian Patent 1,259,149 discloses dental restorative composition containing monofunctional monomer. Howard et al in Canadian Patent 1,102,039 discloses radiation curable coating compositions containing unsaturated addition—polymerizable urethane resin. Suling et al in Canadian Patent 1,145,880 discloses moulded dental pigments. Denyer et al in Canadian Patent 1,148,294 discloses dental compositions Ikeda et al in Canadian Patent 1,149,538 discloses curable resin compositions. Ratcliffe et al in Canadian Patent 1,189,996 discloses polymerizable dental composition containing a mixture of fine particle size and large particle size fillers. Fellmann et al in Canadian Patent 1,200,046 discloses permanent dental restorative material. Michl et al in Canadian Patent 1,209,298 discloses photopolymerizable composition especially for dental purposes. Ibsen et al discloses in Canadian Patent 1,243,796 dental composite and porcelain repair. Ibsen et al in Canadian Patent 1,244,177 discloses methacrylate functional resin dental composite and porcelain repair compositions. Schaefer in Canadian patent 1,244,581 discloses priming material for plastic dental members. Randklev in Canadian Patent 1,245,437 discloses radiopaque low visual opacity dental composites containing non-vitreous microparticles. Waknine in Canadian patent 1,262,791 discloses two component (Paste-Paste) self curing dental restorative material. Okada et al in Canadian Patent Application 2,002,017 discloses dental restorative material. Held et al in Canadian Patent Application 2,009,471 discloses hybrid plastic filling material. Mitra et al in Canadian Patent Application 2,032,773 discloses dental compositions, a method of making shaped dental articles via photoiniferter polymerization of the dental compositions, and shaped dental articles produced thereby. Holmes in Canadian Patent Application 2,033,405 discloses dental material containing anti-slump additive. Rheinberger in Canadian Patent Application 2,051,333 discloses polymerizable dental material. Tateosian et al in European Patent Application 0 334 256 A2 discloses dental appliance preparation and material therefor. Muramoto et al in European Patent Application 0 185 431 A3 discloses composite resin particles, its preparation and resinous composition for coating use containing the same. Kuboto et al in U.K. Patent Application GB 2,189,793A discloses Polymerizable compositions for dental restoration. Heynold et al in PCT/DE87/00135 discloses polymerizable mass for production of non-hardening moulded elements, particular of dental prostheses. Luxatemp—Automix discloses a cartridge for polymerization. DMG HAMBURG discloses paste containing cannulas. Dentsply and Caulk each discloses impression material in a cartridge system having a static mixer.

Typically prior art dentures are produced by combination of polymerizable methacrylate monomers and a polymeric organic filler such as polymethylmethacrylate and its copolymers, which may be superficially soluble in the monomer. These combinations of monomers and polymers are pasty dough-like and polymerize in a mold using peroxides and heat and/or a reducing agent to catalyze the polymerization. Prior art dentures are also commonly produced from paste-like combinations of polymerizable methacrylate monomers, oligomers or prepolymers and organic and inorganic fillers. They may be shaped free-form on a model or polymerized in a mold. A disadvantage of prior art photopolymerizable dental composites is their relatively low degree of conversion to polymer.

Air entrapment during spatulation and mixing is detrimental to strength and provides sites for bacterial colonies, stain and plaque to form. Air dissolved in a free radical polymerizable composition is necessary for premature polymerization inhibitors such as butylated hydroxytolune (BHT) to function to stabilize the material.

It is an object of the invention to provide a means to prepare redox and photoredox polymerized dental prosthesis especially dentures, denture relines, dental crowns, dental bridges and dental restorative materials which are readily formed in a dental laboratory or office.

It is an object of the invention to provide a dispensing system for mixing two paste compositions to produce substantially porosity free dentures and denture relines, dental crowns, dental bridges and dental restorative materials.

It is an object of the invention to provide substantially color stable and porosity-free redox and photoredox polymerized dentures, denture relines, dental crowns, dental bridges and dental restorative materials.

It is an object of the invention to provide a device for forming a dental product including two oxygen permeable containers enclosing polymerizable paste compositions, one of which includes a peroxide and at least one polymerizable acrylic compound.

It is an object of the invention to form a dental product by static mixing of two complimentary pastes one of which includes a peroxide and an acrylic polymerizable compound and the other includes a reducing agent for the peroxide and a polymerizable acrylic compound and then forming and curing the dental product.

As used herein "shelf life" at a specified temperature refers to the time for degradation as discussed in Accelerated Degradation Testing by G. Fagain, H. Sheehan and R. O. Kennedy, *American Biotechnology Laboratory* Volume 9, #9, pages 31–32, October 1991.

As used herein "solvent" refers to compounds in which free radical polymerizable acrylic compounds dissolve, such as t-butyl alcohol, but which are not free radical polymerizable acrylic compounds.

As used herein "radiation" refers to electromagnetic radiation including visible and ultraviolet light, microwave and/or infrared electromagnetic radiation.

As used herein "acrylic" includes compounds of substituted acrylic moieties such as methacryl, cyanoacryl and fluoroacryl-moieties.

As used herein "dental products" includes dental appliances and dental prostheses.

As used herein "dental appliances" means dental products for use in the mouth including orthodontic devices for example devices for movement of teeth.

As used herein "temporary crown" refer to crowns which effectively resist discoloration, detachment and/or breakage for about three weeks.

As used herein "temporary bridge" refer to bridges which effectively resist discoloration, detachment and/or breakage for about three weeks.

As used herein "provisional crown" refer to crowns which effectively resist discoloration, detachment and/or breakage for about one year.

As used herein "provisional bridge" refer to bridges which resist discoloration, detachment and/or breakage for about one year.

SUMMARY OF THE INVENTION

A method of forming dental products, such as dentures, denture relines, dental crowns, dental bridges and dental restorative materials, temporary crown, temporary bridge, provisional crown or provisional bridge, from two polymerizable paste compositions each having a complimentary component of a free radical catalyst system and a polymerizable acrylic compound. One of these paste compositions includes an oxidizing agent and a stabilizer and the other includes a reducing agent as components of a redox catalyst system for free radical polymerization. These paste compositions are mixed in a static mixer to form a polymerizing paste composition, which is then shaped into a dental prosthesis. A handheld mixing dispenser useful in carrying out this method, includes a static mixing conduit, and two containers enclosing the polymerizable paste compositions. The static mixing conduit encloses a static mixing member. The containers are adapted to be connected in fluid flow communication with the static mixing conduit. In the paste composition which includes the reducing agent a photoinitiator may be preferably included. Each container is sufficiently oxygen permeable to maintain inhibition of polymerization of the polymerizable paste composition therein for at least 12 months at 23° C.

DETAILED DESCRIPTION OF THE INVENTION

Figure 1:
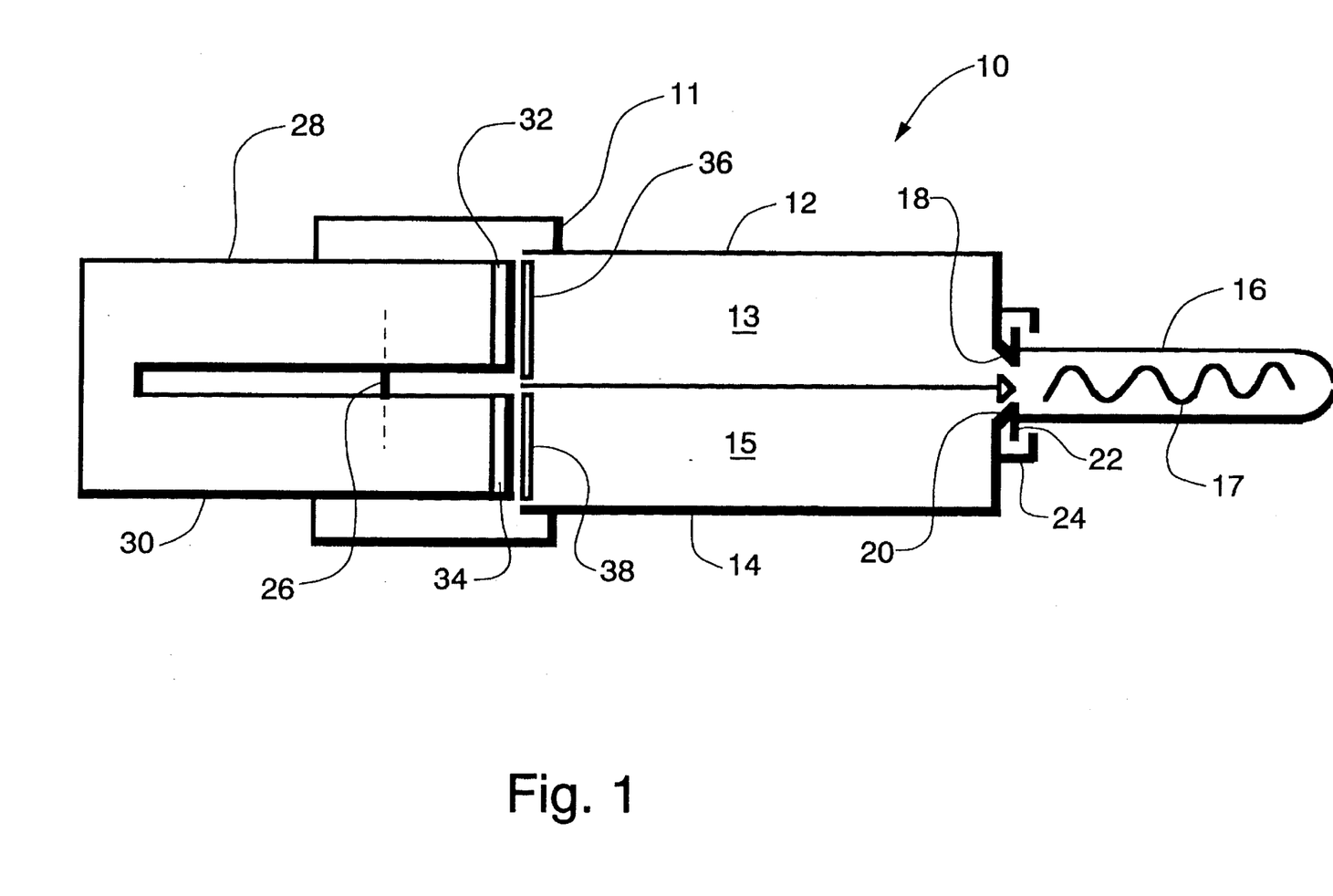
FIG. 1 is a schematic top view of a static mixing article of manufacture in accordance with the invention.
Figure 2:
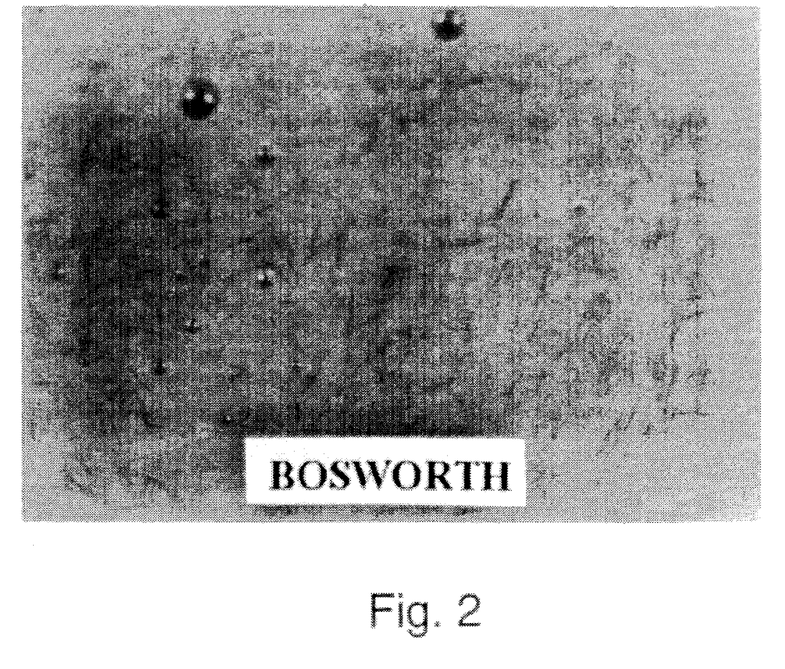
FIG. 2 is a photographic enlargement (3.4 times actual size) of a portion of the prior art Bosworth product shown in FIG. 7.

The invention is now described with more particular reference to FIG. 1 which shows a dispenser article 10 in accordance with the invention having housing 11 which supports an oxygen permeable cylindrical container 12 enclosing catalyst containing polymerizable paste composition 13, and oxygen permeable cylindrical container 14 enclosing accelerator containing polymerizable paste composition 15. Preferably the containers are cylindrical and have a wall thickness of from about 0.1 to about 2 min. Containers 12 and 14 are connected to mixing channel 16 which encloses a static mixing member 17 having a series of baffles turned at angles that cause the two streams from conduits 18 and 20 to divide and recombine and mix. Mixing channel 16 is in fluid flow communication with containers 12 and 14 through conduits 18 and 20 respectively. Mixing channel 16 is connected to housing 11 by interlocking flanges 22 and 24. Containers 12 and 14 are filled with polymerizable paste compositions 13 and 15 respectively without including of air by entrapment. Preferably compositions 13 and 15 are extruded at a predetermined rate into static mixing channel 16 where they are combined essentially without inclusion of air by entrapment to form a polymerizing composition which is readily modeled and/or molded. Additional mixing, such as on a slab or in a bowl, is not required.

In use the operator presses actuator 26 which forces rods 28 and 30, which support plungers 32 and 34, into containers 12 and 14. Plungers 32 and 34 press against disc shaped end walls 36 and 38 respectively. End walls 36 and 38 press upon polymerizable compositions 13 and 15 forcing them through conduits 18 and 20 into mixing channel 16. Polymerizable paste compositions 13 and 15 each contain a component of a polymerization catalyst system which upon mixing provides a free radical generating catalyst system. Polymerizable accelerator paste composition 15 includes a reducing agent and in a preferred embodiment a radiation activated initiator, and at least one polymerizable compound. The catalyst paste composition 13 includes an oxidizer and at least one polymerizable compound. Polymerizable paste compositions 13 and 15 are extruded simultaneously through a static mixing channel 16. The polymerizable compositions 13 and 15 are mixed by static mixing member 17 and form a polymerizing composition which is readily molded to a dental prosthesis. In a preferred embodiment, further polymerization of the molded composition may be then accomplished by application of external energy such as light, microwaves, heat, and/or by additional redox polymerization.

Preferably the polymerizable paste compositions 13 and 15 each contain at least 10% filler, have a viscosity of at least 5000 centipoise (cps) and are substantially solvent free i.e., have less than 1 percent by weight solvent, more preferably less than 0.5 percent by weight solvent and most preferably do not include a solvent. Polymerizable paste compositions 13 and/or 15 preferably includes a filler and polymerizable (meth)acrylate compound.

In a preferred embodiment of the invention a dispenser device includes two connected syringe tubes each having a plunger. The plungers are connected for simultaneous actuation by the operator to discharge the pastes simultaneously through a third discharge tube containing a static mixing element to form a polymerizing paste having dissolved air in a concentration which is insufficient to result in visible voids in the polymerized product formed by the polymerizing paste composition.

In a preferred embodiment compositions of the invention are used to reline dentures. Polymerizable pastes are statically mixed to form a polymerizing reline paste composition which is extruded directly onto a denture which is being relined to better fit the changed soft tissue contours of the mouth of the patient since the denture was originally produced, or to otherwise improve the fit of the denture to the patients mouth. Air is not entrapped within the statically mixed polymerizing reline paste composition as it would be if the polymerizable pastes had been mixed by stirring or spatulation. The polymerizing reline paste composition is adapted (shaped) to areas to be impressed. The polymerizing reline paste composition is readily modeled with a gloved finger or suitable tool. An impression of the mouth is made in the polymerizing reline paste composition after it is mixed but before it is no longer impressionable, which defines the work time. The polymerization catalyst is activated during the mixing. The polymerizing reline paste composition preferably has a work time of less than about 5 minutes. Within minutes the extruded polymerizing composition is partially polymerized and hardened. The exotherm of the polymerizing composition is lower than it would be if substantially all of the monomer had been more rapidly converted to polymer. The temperature of the exotherm of polymerizing composition is easily tolerated without discomfort to the patient. In a preferred embodiment the reline composition is further polymerized extraorally using a dental light curing oven which provides heat and light. In a preferred embodiment of the invention a mouth molded partially polymerized reline composition adhered to a denture is placed after impressing into a TRIAD® 2000 light curing oven (sold by Dentsply International Inc.) for from 1 to 20 minutes to additionally polymerize the reline composition. Alternatively, a partially converted reline composition adhered to a denture is invested in plaster or other media to retain its shape and heated to thermally more completely convert and cure reline composition. In another embodiment of the invention partially polymerized reline composition and the denture adhered to it are removed from the patient's mouth and further cured under vacuum, pressure in air, water, nitrogen or other inert liquid and/or gas filled container at elevated temperature to substantially complete cure, convert and polymerize the composition. One advantage of this method of packaging, mixing and conversion to cured article is that, because concentrations of amine or other potential color forming reducing agents are low, the potential for unwanted color formation during or after polymerization in minimized.

In another preferred embodiment of the invention the polymerizing paste composition is extruded directly into a preformed mold cavity. The mold is preferably formed by the lost "wax" or other mold making process. The polymerizing paste is extruded under pressure and polymerized within the mold at ambient temperatures or with the application of heat or light to accelerate polymerization to form a dental prosthesis, such as a denture or crown and bridge element.

In another preferred embodiment of the invention a polymerizing paste composition is extruded from the static mixer into a tray and applied directly onto the patients tissue and modeled to form a custom tray. Alternatively a polymerizing paste is extruded on a model of a patient's tissues to form an impression tray, or a dental prosthesis. In another embodiment a polymerizing paste is extruded directly onto the teeth and a bite registration impressed therein, or it is used to repair a prosthesis which is fixed in the patients mouth. These methods are convenient for deposition of the polymerizing composition at the site of use and provide dental products which are lower in porosity and therefor more stain resistant than if mixed by hand spatulation. In all these applications the product which results is rigid, with a modulus of elasticity greater than about 100,000 psi.

Preferred monomers, oligomers and prepolymers for use in accordance with the invention include polyester and polyether methacrylates, urethane methacrylate, and polyglycol methacrylate(s). Polymerizable methacrylates are waxy, syrupy or mobile liquids. In a preferred embodiment each polymerizable paste composition includes a methacrylate monomer, oligomer, or prepolymer such as Uvithane 783, 893 or 892 (sold by Morton International) or Craynor CN 961, 962, 964, 966, 971 or 973 (sold by Sartomer) Mhoromer 6661-0 (sold by Rohm Tech.) and an organic filler and an inorganic filler.

Polymerizable acrylic compounds useful in accordance with the invention include compounds within the scope of general formula (I):

wherein R is an acrylic-free organic moiety, $R_1$ is hydrogen, halogen, alkyl, substituted alkyl or cyano radical and n is an integer from 1 to 6 and m is an integer from 1 to 1000.

R is a hydrocarbyl spacer unit such as alkyl or aromatic or polyether, polyurethane, polyester, glycol, polyglycol including forms thereof substituted with carboxyl, phosphoric and other acid moieties and salts thereof.

Examples of unsaturated acrylic compounds containing phosphorus and phosphonic acid esters which may be used as polymerizable acrylic compounds useful in accordance with the invention include, but are not limited to, monomers containing phosphoric acid groups such as hydroxyethyl methacrylate monophosphate, 2,2'-bis(alpha-methacryloxy-beta-hydroxypropoxyphenyl)propane diphosphonate (BIS-GMA diphosphonate), BIS-GMA methacryloxyethyl phosphate, glyceryl dimethacrylate monofluorophosphate, and glyceryl dimethacrylate phosphate. Preferred compounds are those polyethylenically unsaturated monophosphates of the formula (III):

and salts thereof, in which R is an organic radical having a valency of n+1; and R may be interrupted by one or more oxygen atoms and may be substituted or unsubstituted, and may comprise an aliphatic radical, or a cycloaliphatic radical, or an aryl radical; $R_1$ is as defined above and n is an integer of at least 1.

Polymerizable acrylic compounds useful to provide polymerizable paste compositions in accordance with the invention include monofunctional monomers and multifunctional oligomers and/or monomers having di- or polyfunctional moieties which are capable of addition polymerization. In general, preferred reactive functionalities which serve as active sites for this polymerization are acrylic. Monofunctional monomers include cyclohexyl methacrylate, benzyl methacrylate, methacrylate, t-butyl methacrylate, n-butyl methacrylate, isobutyl methacrylate, and 2-ethylhexyl methacrylate. Suitable multifunctional monomers and oligomers may be selected from numerous families of polyfunctional vinyl and/or addition polymerizable monomers such as acrylic and lower alkyl acrylic acid diesters, acrylic and lower alkyl acrylic acid esters formed from alcohols, which alcohols have a different reactive functional group, such as carboxyl and hydroxyl groups, urethane diacrylates and dimethacrylates, polyvinylic compounds, divinyl aromatic compounds, and others as will be apparent to those skilled in the art.

Preferred, multifunctional monomers and oligomers useful as polymerizable acrylic compounds in polymerizable paste compositions of the invention include esters of unsaturated acids, e.g., acrylic, methacrylic, ethacrylic, propacrylic, butacrylic, maleic, fumaric, citraconic, mesaconic, itaconic, malonic, or aconitic, acids. Other unsaturated acids will be readily apparent to those skilled in the art. These acids are preferably reacted with either saturated or unsaturated polyhydroxylic alcohols to form esters which are effective multifunctional monomers and oligomers useful in the formulation of the compositions of the invention. In general, these alcohols have one or more hydroxylic functionality and have from 2 to about 30 carbon atoms. Thus, useful alcohols include allyl, methallyl, crotyl, vinyl, butenyl, isobutenyl, and similar unsaturated alcohols as well as polyols such as ethylene glycol, propylene glycol, butylene glycol, diethylene glycol, triethylene glycol, tetraethylene glycol, pentaethylene glycol, glycerol, 1,3,3-trimethylolpropane, pentaerythritol, dihydroxyphenol, and alkylidene bisphenols such as bisphenol-A, 1,1-bis (4-hydroxyphenyl) methane, 4,4'-dihydroxybiphenyl, 4,4'-dihydroxydiphenyl sulfone, dihydroxydiphenyl ether, dihydroxydiphenyl sulfoxide, resorcinol, hydroquinone, etc.

Preferred multifunctional monomers and oligomers useful as polymerizable acrylic compounds in polymerizable paste compositions of the invention include the esters of a monomeric unsaturated acids with an unsaturated mono-hydroxylic alcohol such as allyl acrylate, allyl methacrylate, dimethallyl fumarate, N-allyl acrylamide, crotyl acrylate, allyl crotonate, allyl cinnamate and diallyl maleate. Other preferred species are the di-, tri-, and higher esters of polyhydroxylic alcohols such as ethylene glycol diacrylate (dimethacrylate and C2–C6 homologs), trimethylolpropane trimethacrylate, and the dimethacrylate ester of bisphenol-A as well as other acrylate and alkyl acrylate esters. Furthermore, mixtures of multifunctional monomers and/or oligomers are useful in the practice of the invention.

Polymerizable acrylic compounds such as bis-GMA and the urethane dimethacrylate formed from the reaction of hydroxyethyl acrylate, hydroxypropyl acrylate, and their methacrylate homologs with 2,2,4-trimethylhexyl-1,6-diisocyanate (hereinafter referred to as "urethane dimethacrylate" or "diacrylate") are especially useful, as are ethylene glycol dimethacrylate, 1,6-hexanediol dimethacrylate trimethylolpropane trimethacrylate and the dimethacrylate ester of bisphenol-A and urethane adducts thereof. The corresponding acrylates are similarly useful as is diallyl maleate.

In a preferred aspect of the invention, polymerizable acrylic compounds useful in accordance with the invention are vinyl urethane or urethane(meth)acrylate monomer or prepolymer materials characterized by the structural formula (II):

wherein each R1 independently, is $R_1$ is hydrogen, halogen, alkyl, substituted alkyl or cyano radical R2 and R4, independently, are alkylene, substituted alkylene, cycloalkylene, substituted cycloaklylene, arylene or substituted arylene; and, R3 is alkylene, substituted alkylene, cycloalkylene, arylene, substituted arylene, heterocyclic, substituted heterocyclic, the reaction product of an organic diisocyanate or an isocyanate terminated prepolymer and a compound having hydroxyl functionality, or the reaction product of a polyol or a hydroxyl terminated prepolymer and a compound having isocyanto functionality.

Preferred rubber modifiers for use in polymerizable compositions in accordance with the invention include acrylic rubber modifier (Paraloid KM 334 manufactured by Rohm and Haas) and methacrylated butadiene-styrene rubber (Metablen C223 produced by Elf Atochem).

A preferred stabilizer is butylated hydroxytoluene.

Preferred fillers useful in the paste compositions of the invention include organic fillers such as particulate polymer, and inorganic filler such as glass, ceramic, or glass ceramic. Preferably the filler has a particle size of less than about 200 μm, more preferably less than about 100 μm and most preferably less than about 35 μm. Organic fillers include natural and synthetic polymers and copolymers which preferably are formed by, emulsion polymerization, bulk polymerization or suspension polymerization. The fillers may be comminuted by ball milling, shearing or by atomization. Inorganic fillers are produced by fusion or sol gel techniques and may be comminuted by ball milling, attritor milling atomization, attention milling or precipitation. Preferred inorganic fillers include silica, quartz, borosilicates, silicious fillers, inorganic glasses, such as barium aluminum silicate, lithium aluminum silicate, strontium, lanthanum, and tantalum aluminosilicate glasses. A preferred inorganic filler is microfine amorphous silicone dioxide particulate. Silanated inorganic fillers are considered for purposes of this invention to be inorganic fillers and are also preferred. Silanated means that some of the silanol groups have been substituted or reacted with, for example, dimethyldiclorosilane to form a hydrophobic filler.

Preferably the polymerizable compositions mixed in accordance with the invention have substantially the same viscosity. Preferably the polymerizable compositions are mixed in a volume ratio between 1:1 and 1:5. More preferably the polymerizable compositions are mixed in a volume ratio between 1:1 and 1:3. Most preferably the polymerizable compositions are mixed in a 1:1 volume ratio. Preferably each container has an oxygen permeability coefficient at least about $0.4 \times 10^{-10}$ cm$^2$/sec (cm Hg). Preferably each polymerizable paste composition in each container has a shelf life of at least 180 days. Preferred microwave activated catalyst systems include benzopinacole or tertiary butyl perisononanoate. Preferably dental products made in accordance with the invention have a specific gravity at least 0.5% greater than a corresponding product formed by hand spatulation of said polymerizable paste compositions, and forming and curing the spatulated paste composition.

Prior Art: Astron

EXAMPLE 1

Figure 4:
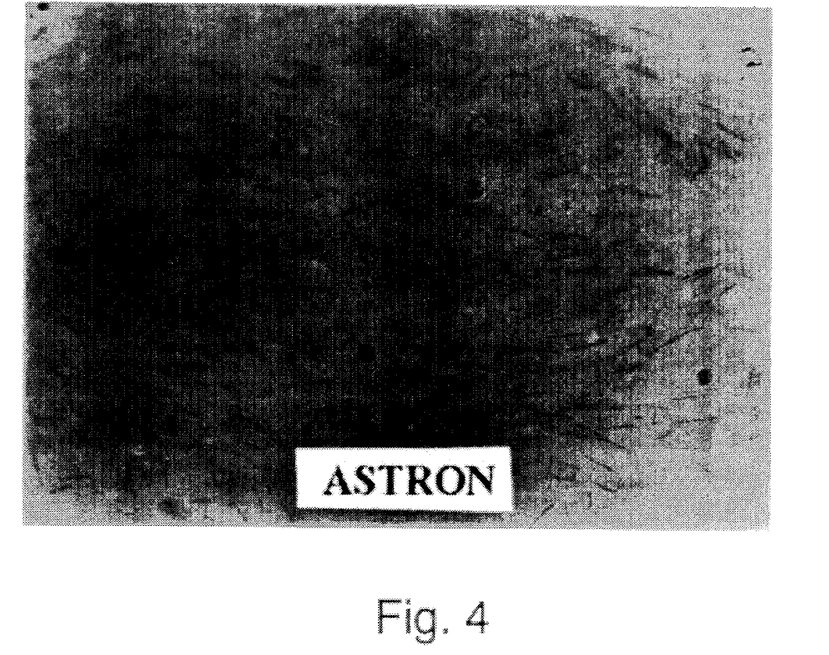
FIG. 4 is a photographic enlargement (3.4 times actual size) of a portion of the prior art Astron product shown in FIG. 7.

Powder and liquid are mixed in a ratio of 2.5 cm$^3$/ml in accordance with the instructions of the manufacturer of Astron LC reline: Astron Dental Corp. Wheeling, Ill. to form a paste which is placed in a mold and covered by a polyethylene film and allowed to stand for 5 minutes and then light cured for 5 minutes in an Astron XL (sold by Astron Dental Corp.) light curing unit to form a disk. A 3.4 times actual size photographic enlargement of the disk is shown in FIG. 4. These powder and liquid compositions are described by Smith et al in the International Journal of Prosthodontics Volume 4 Number 1991 pages 445–448. The powder includes poly(ethyl methacrylate), peak mw 245, 488, and 1.0% benzoyl peroxide. The liquid includes: n-butyl methacrylate, ethoxylated bis phenol A dimethacrylate, dimethyl-para-toluidine and camphorquinone.

Prior Art: Extoral

EXAMPLE 2

Figure 3:
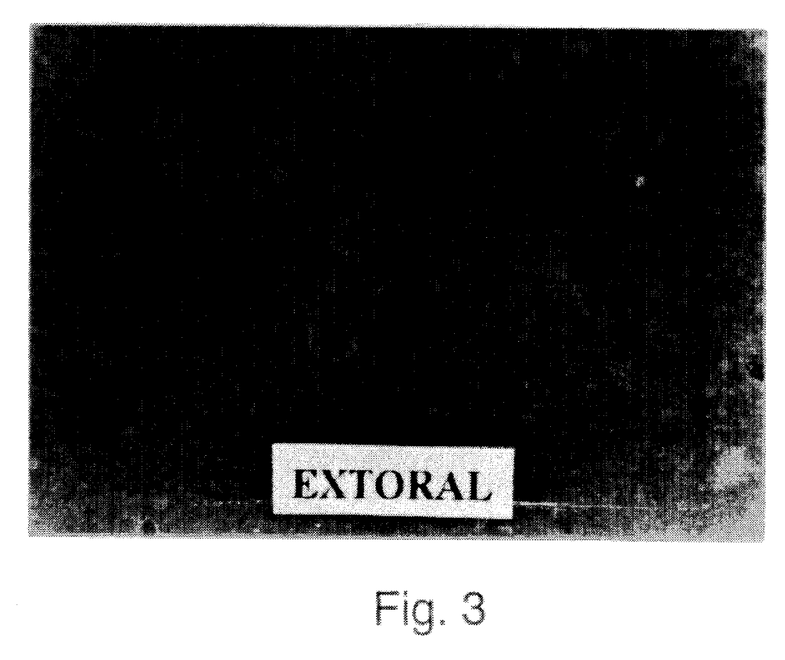
FIG. 3 is a photographic enlargement (3.4 times actual size) of a portion of the prior art Extoral product shown in FIG. 7.

Powder and liquid are mixed in a ratio of 2.0 cm$^3$/ml in accordance with the instructions of the manufacturer of Extoral reline material: Pro-Den Systems Portland, Ore. to form a paste which is placed in a mold and covered by a polyethylene film and allowed to stand for 5 minutes and then light cured for 5 minutes in a Star Cure 360 (sold by Star Dental) light curing unit to form a disk. A 3.4 times actual size photographic enlargement of the disk is shown in FIG. 3.

These powder and liquid compositions are described by Smith et al in the International Journal of Prosthodontics Volume 4 Number 1991 pages 445–448. The powder includes: poly(ethyl methacrylate)/poly(methyl methacrylate) copolymer (9/1), peak mw 381.987; 0.9% benzoyl peroxide. The liquid includes: 67.1% ethoxylated bisphenol A dimethacrylate 30.1% cyclohexyl methacrylate, 0.14% camphorquinone. The cured material includes 2.83% inorganic filler, (see Barron et al, Dent Mater 8:27–277, July 1992 pages 274–277 at page 276.

Prior Art: Bosworth

EXAMPLE 3

Figure 6:
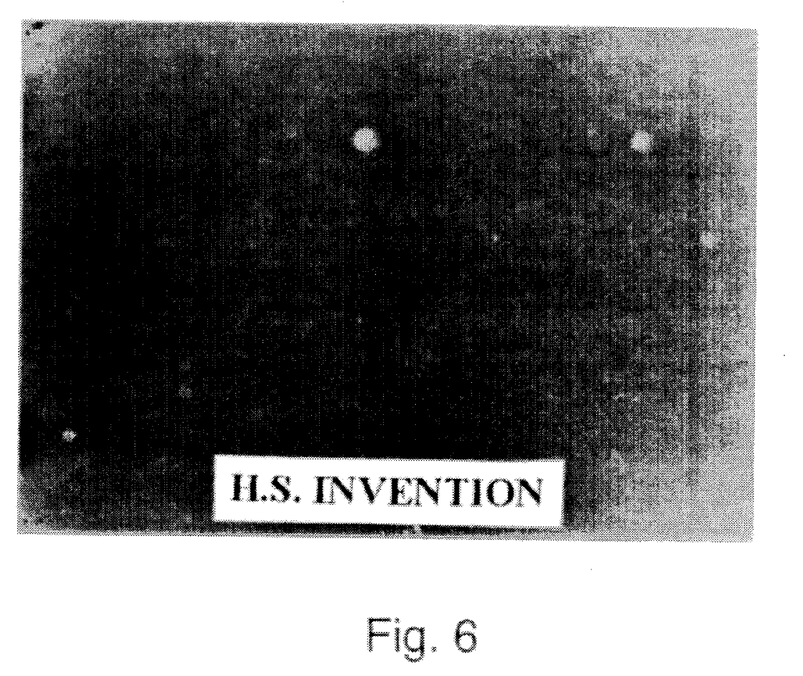
FIG. 6 is a black and white photographic enlargement of a portion of a product formed by hand spatulation (H.S.) of the composition used in the invention shown in FIG. 7.

Powder and liquid are mixed in a ratio of 1.9 cm$^3$/ml in accordance with the instructions of the manufacturer Bosworth Reline material: Harry J. Bosworth Skokie, Ill. to form a paste which is placed in a mold and covered by a polyethylene film and allowed to stand for 5 minutes and then light cured for 5 minutes in an Pro Lite 3 (sold by Pro Den Corporation) light curing unit to form a disk. A 3.4 times actual size photographic enlargement of the disk is shown in FIG. 6. These powder and liquid compositions are described by Smith et al. The powder includes poly(ethyl methacrylate), peak mw 300, 312; and 0.9% benzoyl peroxide. The liquid includes 13.9% n-butyl methacrylate; 74.1% ethoxylated bisphenol A dimethacrylate; dimethyl-para-toluidine and 0.16% camphorquinone.

Catalyst Paste

EXAMPLE 4

A catalyst paste is formed by mixing in a planetary mixer 4210 g 7,7,9-trimethyl-4,13-dioxo-3,14-dioxa-5,12 -dioldimethacrylate, 0.7 g 3-methacryloxypropyltrimethoxysilane, 3.5 g butylated hydroxytoluene, 70 g benzoyl peroxide, and 2715 g powder blend. The powder blend is formed by mixing 3270 g fumed silica inorganic filler, 32920.7 g poly(methyl methacrylate-co-ethylene glycol dimethacrylate-co-ethyl methacrylate-styrene) (49.2:0.8:34.0:16.0) and 10 g pigment. This paste composition is stored in a chamber of a polypropylene cartridge tube having a wall thickness of 1 mm in a dual cartridge used in a hand activated dispenser made by MixPac.

| CATALYST PASTE | |
|---|---|
| | Percent by Weight |
| 7,7,9-Trimethyl-4,13-dioxo-3,14-dioxa-5,12-dioldimethacrylate | 60.15 |
| 3-Methacryloxypropyltrimethoxysilane | 0.01 |
| Butylated hydroxytoluene | 0.05 |
| Benzoyl Peroxide | 1.00 |
| Fumed silica inorganic filler | 3.50 |
| Poly (methyl methacrylate-co-ethylene glycol dimethacrylate-co-ethyl methacrylate-styrene) (49.2:038:34.0:16.0) | 35.26 |
| Pigment | 0.03 |
| | 100.00 |

Accelerator and Radiation Cure Initiator Paste

EXAMPLE 5

An accelerator and radiation cure initiator paste is formed by mixing in a planetary mixer 216.5 g 7,7,9-trimethyl-4,13-dioxo-3,14-dioxa-5,12-dioldimethacrylate, 0.036 g 3-methacryloxypropyltrimethoxysilane, 0.05 g butylated hydroxytoluene, 0.65 g camphorquinone 1.08 g (2-hydroxy-4-methoxyphenyl) benzophenone, 0.9 g dihydroxyethyl-p-toluidine and 140.75 g of powder blend formed as described in Example 4, in a planetary mixer. This paste composition is stored in the other chamber of the polypropylene cartridge of the dispenser used in Example 4. It has the composition shown in Table 1.

Accelerator and Radiation Cure Initiator Paste

EXAMPLE 6

An accelerator and radiation cure initiator paste is formed by mixing in a
mixer planetary 216.5 g 7,7,9-trimethyl-4,13-dioxo-3,14-dioxa-5,12-dioldimethacrylate, 0.036 g 3-methacryloxypropyltrimethoxysilane, 0.05 g butylated hydroxytoluene, 0.65 g camphorquinone 1.08 g (2-hydroxy-4-methoxyphenyl) benzophenone, 1.8 g dihydroxyethyl-p-toluidine and 140.75 g of powder blend formed as described in Example 4. This paste composition is stored in a chamber of a polypropylene cartridge tube of a dispenser prepared as described in Example 4. It has the composition shown in Table 1.

TABLE 1

Accelerator and radiation cure initiator paste compositions

|  | Example 5 Percent by Weight | Example 6 Percent by Weight |
|---|---|---|
| 7,7,9-Trimethyl-4,13-dioxo-3,14-dioxa-5,12-dioldimethacrylate | 60.33 | 60.10 |
| 3-Methacryloxypropyltrimethoxysilane | 0.01 | 0.01 |
| butylated hydroxytoluene | 0.01 | 0.01 |
| Camphorquinone | 0.18 | 0.18 |
| Dihydroxyethyl-p-toluidine | 0.25 | 0.50 |
| Fumed Silica | 3.54 | 3.53 |
| Poly (methyl methacrylate-co-ethyleneglycol dimethacrylate-co-ethyl methacrylate-styrene) (49.2:038:34.0:16.0) | 35.68 | 35.66 |
| Pigment | 0.01 | 0.01 |

Static Mixed Redox and Light Cured Denture Reline

EXAMPLE 7

Figure 5:
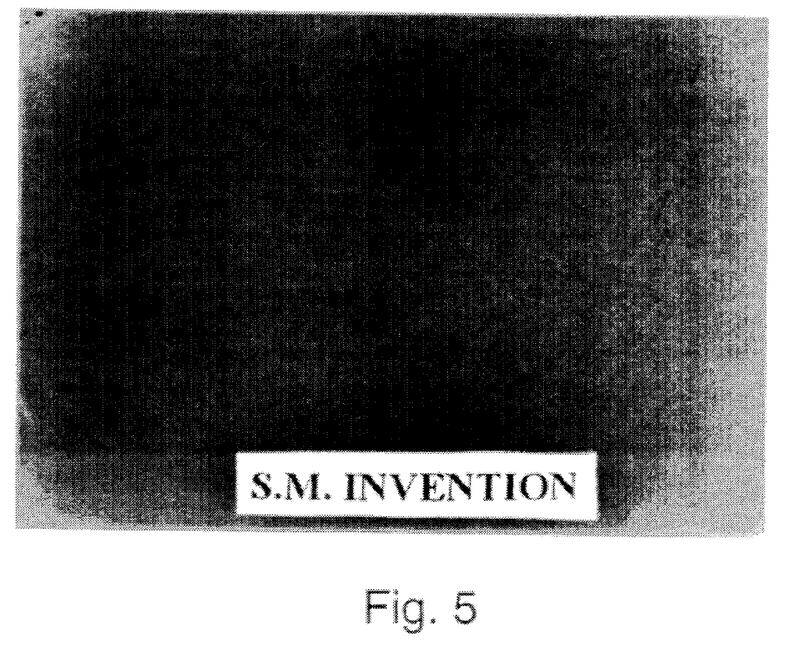
FIG. 5 is a photographic enlargement (3.4 times actual size) of a portion of the static mixed (S.M.) product of the invention shown in FIG. 7.

10 g of catalyst paste formed as described in Example 4 is mixed in the static mixer with 10 g of accelerator and radiation cure initiator paste formed as described in Example 5 to form 20 g of a denture reline composition. The polymerizing denture reline composition contains 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyltrimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g camphorquinone, 0.15 g (2-hydroxy-4-methoxyphenyl) benzophenone, and 0.125 g dihydroxyethyl-p-toluidine. The polymerizing composition is extruded from the static mixer and placed upon a denture surface, after 2 minutes the denture is positioned in a patients mouth and allowed to cure for 3 minutes. A portion of the polymerizing composition is formed into a disk. A 3.4 times actual size photographic enlargement of the disk is shown in FIG. 5. The denture is then removed and radiation cured in a TRIAD 2000 light curing unit for 5 minutes. See Table 7 for formula percentages and properties ingredient.

Static Mixed Redox and Light Cured Denture Reline

EXAMPLE 8

10 g of catalyst paste formed as described in Example 4 is mixed in the static mixer with 10 g of accelerator and radiation cure initiator paste formed as described in Example 6 to form 20 g of a denture reline composition. The polymerizing denture reline composition contains 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyltrimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g camphorquinone, 0.15 g (2-hydroxy-4-methoxyphenyl) benzophenone, and 0.25 g dihydroxyethyl-p-toluidine. The polymerizing composition is placed upon a denture surface, after 2 minutes the denture is positioned in a patients mouth and allowed to cure for 3 minutes. The denture is then removed and radiation cured in a TRIAD 2000 light curing unit for 5 minutes. See Table 7 for formula ingredient percentages and properties.

Hand Spatulation Denture Reline Composition

EXAMPLE 9

10 g of the paste composition formed as in Example 4 and 10 g of the paste composition formed as in Example 5 are mixed by hand until homogenous upon a parchment pad using a spatula to form a polymerizing composition, which is shaped into a disk. A 3.4 times actual size photographic enlargement of the disk is shown in FIG. 6. See Table 7 for properties.

Hand Spatulation Redox and Light Cured Denture Reline

EXAMPLE 10

10 g of the paste composition formed as in Example 4 and 10 g of the paste composition formed as in Example 6 are mixed by hand on a pad using a spatula to form a polymerizing composition. Portion of the polymerizing composition placed upon a denture surface, after 2 minutes the denture is positioned in a patients mouth and allowed to cure for 3 minutes. The denture is then removed and radiation cured in a TRIAD 2000 light curing unit for 5 minutes. See Table 7 for properties.

Static Mixed Redox and Light Cured Denture

EXAMPLE 11

10 g of catalyst paste formed as described in Example 4 is mixed in the static mixer with 10 g of accelerator and radiation cure initiator paste formed as described in Example 5 to form 20 g of a denture reline composition. The polymerizing denture reline composition contains 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyl-trimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g camphorquinone, 0.15 g (2-hydroxy-4-methoxyphenyl) benzophenone, and 0.125 g dihydroxyethyl-p-toluidine. The polymerizing composition is extruded through a static mixer and placed in a denture mold half, after 2 minutes the denture mold halves are positioned together and allowed to cure for 10 minutes. The denture is then removed and radiation cured in a TRIAD 2000 light curing unit for 5 minutes.

Static Mixed Redox and Light Cured Temporary Bridge

EXAMPLE 12

10 g of catalyst paste formed as described in Example 4 is mixed in the static mixer with 10 g of accelerator and radiation cure initiator paste formed as described in Example 5 to form 20 g of a denture reline composition. The polymerizing denture reline composition has 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyl-trimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g camphorquinone, 0.15 g (2-hydroxy-4-methoxyphenyl) benzophenone, and 0.125 g dihydroxyethyl-p-toluidine. The polymerizing composition is placed in mold created by vacuum molding a sheet of thermoplastic polystyrene over a model of a dentition to be replicated and allowed to cure for 5 minutes. The temporary bridge is then removed from the mold and radiation cured in a TRIAD 2000 light curing unit for 10 minutes.

Static Mixed Redox and Light Cured Crown

EXAMPLE 13

10 g of catalyst paste formed as described in Example 4 is mixed in the static mixer with 10 g of accelerator and radiation cure initiator paste formed as described in Example 5 to form 20 g of a denture reline composition. The polymerizing denture reline composition has 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyl-trimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g camphorquinone, 0.15 g (2-hydroxy-4-methoxyphenyl) benzophenone, and 0.125 g dihydroxyethyl-p-toluidine. The polymerizing composition is extruded from a static mixer into an alginate impression, placed in the mouth and allowed to cure for 5 minutes. The temporary crown is then removed from the mold and radiation cured in a TRIAD 2000 light curing unit for 5 minutes.

Static Mixed Redox and Microwave Cured Denture

EXAMPLE 14

10 g of catalyst paste formed as described in Example 4 is mixed in the static mixer with 10 g of accelerator and radiation cure initiator paste formed as described in Example 5, except that benzopinacole is substituted for camphorquinone, to form 20 g of a denture reline composition. The polymerizing denture reline composition has 0.5 percent by weight benzoyl peroxide. 60.12 g 7,7,9-trimethyl-4,13-dioxo-3,14-dioxa-5,12-diazahexadecane-1,16-dioldimethacrylate (UDMA), 0.01 g 3-methacryloxypropyl-trimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.09 g benzopinacole, 0.15 g (2-hydroxy-4-methoxyphenyl) benzophenone, and 0.125 g dihydroxyethyl-p-toluidine. The polymerizing composition is extruded through a static mixer and placed in a prepared denture mold with teeth embedded in one half, after 2 minutes the denture mold halves are pressed together and allowed to cure for 15 minutes. The denture mold is then removed from the metal flask and post-cured in a 50.0 watt microwave curing oven 5 minutes. The denture is then removed from the mold and polished.

Static Mixed Redox and Heat Cured Denture

EXAMPLE 15

10 g of catalyst paste formed as described in Example 4 is mixed in the static mixer with 10 g of accelerator and radiation cure initiator paste formed as described in Example 5, to form 20 g of a denture composition. The polymerizing denture composition has 0.5 percent by weight benzoyl peroxide, 60.12 g 7,7,9-trimethyl-4,13-dioxo-3,14-dioxa-5,12-diazahexadecane-1,16-dioldimethacrylate (UDMA), 0.01 g 3-methacryloxypropyl-trimethoxysilane, 0.03 g butylated hydroxytoluene, 35.44 g poly(methyl methacrylate-co-ethylene dimethacrylate-co-ethyl methacrylate-co-styrene) (49.2:0.8:34.0:16.0) (cured bead polymer), 3.6 g of silicon dioxide and 0.01 g pigment, 0.15 g (2-hydroxy-4-methoxyphenyl) benzophenone, and 0.125 g dihydroxyethyl-p-toluidine. The polymerizing composition is extruded from a static mixer and placed in a prepared denture mold (with teeth embedded in one half), after 2 minutes the denture mold halves are pressed together and allowed to cure for 10 minutes. The denture flask is then placed in a heat curing unit (hot water bath) at 72.8° C. (163° F.) for 1½ hours followed by ½ hour immersion in boiling water. The denture is then removed from the mold and polished. The molded denture material has a flexural strength of 102 MPa, a flexural modulus of 3120 MPa. The molded denture a deflection (at break) of 6.1 mm and an impact strength of J/m.

The mechanical properties of the heat-cured material are determined by testing the flexural strength and impact strength of rectangular bars (3.18 mm×11.2 mm×85 mm) produced in steel molds. Bars of the denture material are prepared by extruding material into the bar mold cavities, then positioning the top plate and allowing the material to self cure for 10 to 15 minutes. After the initial self-cure, the bar molds (with top and bottom plates) are placed in a spring clamp. The denture material is fully-cured by placing the steel mold into a hot water bath at 72.8° C. (163° F.) for 1½ hours followed by immersion in boiling water for ½ hour. The bars of denture material are then removed from the steel mold and sanded to size with silicon carbide paper (120 grit followed by 400 grit). The final dimensions of each bar is 2.85 mm×10–11 mm×85 mm. The flexural strength properties are determined using an Instron Model 4301 at a crosshead speed of 2.54 mm per minute. The unnotched Izod impact strength is determined on a T. M. I. Impact Test Machine Model 43-01 by using the halves of the 85 mm bar broken in flexure.

Work Time and Set Time Compared for Products Formed by Static and Hand Mixing

Work Time and Set time, measures of the polymerization rate, are shown in Tables 2, 3 and 7 for mixing by static mixing and hand spatulation equal masses of the Catalyst Paste of Example 4 and the Paste of Example 5 or 6, which contain different dihydroxy-p-toluidine concentrations. For static mixing a twelve element static mixer is used. Hand spatulation is carried out on a mix pad. The Work Time is measured as the time when the material no longer peaks up from the surface when probed by a sharp instrument. The Set Time is the time when the sample becomes solid i.e. the probe does not penetrate the surface of the material.

TABLE 2

WORK TIME

| Composition equal volumes of pastes of Example | Dihydroxy-p toluidine (Percent by weight) | Work time using Static Mix (Minutes) | Work time using Hand Spatulation Mix (Minutes) | Difference in work time (percent) |
|---|---|---|---|---|
| 4 and 5 | 0.125 | 3.25 | 6.25 | 92 |
| 4 and 6 | 0.250 | 1.00 | 1.75 | 75 |

TABLE 3

SET TIME

| Composition equal volumes of pastes of Example | Dihydroxy-p toluidine (Percent by weight) | Set time using Static Mix (Minutes) | Set time using Hand Spatulation Mix (Minutes) | Difference in set time (percent) |
|---|---|---|---|---|
| 4 and 5 | 0.125 | 4.25 | 7.25 | 70 |
| 4 and 6 | 0.250 | 1.75 | 2.25 | 29 |

The results in Table 2, 3 and 7 show advantageously faster polymerization rate using the static mix method which avoids the inhibitory effect of excess air incorporated in the polymerizing composition during hand spatulation. The rate of polymerization is most sensitive to the mix method at the lower dihydroxy-p-toluidine level.

Color Stability for Products Formed by Static and Hand Mixing

Preferably dental products in accordance with the invention have a total color change less than 1.0 as measured on the CIELAB scale. The color stability of catalyst and base mixed with the static mixer are compared with hand spatulated material. The color stability test is performed by exposing 50 mm by 0.5 mm disks of the polymerized materials to a sun lamp as designated by American Dental Association Specification No. 12. The color change from the color stability test is measured by CIELAB ΔE total color change with the results shown in Tables 4 and 7:

TABLE 4

COLOR STABILITY
Total Color change (CIELAB ΔE)

| Composition equal volumes of pastes of Examples | Dihydroxy-p-toluidine (Percent by weight) | Static Mix (Total Color Change), ΔE | Hand Spatulation Mix, ΔE (Total Color Change) | Percent Change in Color |
|---|---|---|---|---|
| 4 and 5 | 0.125 | 0.74 | 1.31 | 77 |
| 4 and 6 | 0.250 | 2.04 | 2.34 | 15 |

The total color change ΔE was less than 1 for the static mix material, a change that is not perceptible, at the lower dihydroxy-p-toluidine level. The spatulated polymerizable composition shows perceptible change. The higher dihydroxy-p-toluidine level showed much greater color change for both mix methods.

Air Entrapment in Products Formed by Static and Hand Mixing

Figure 7:
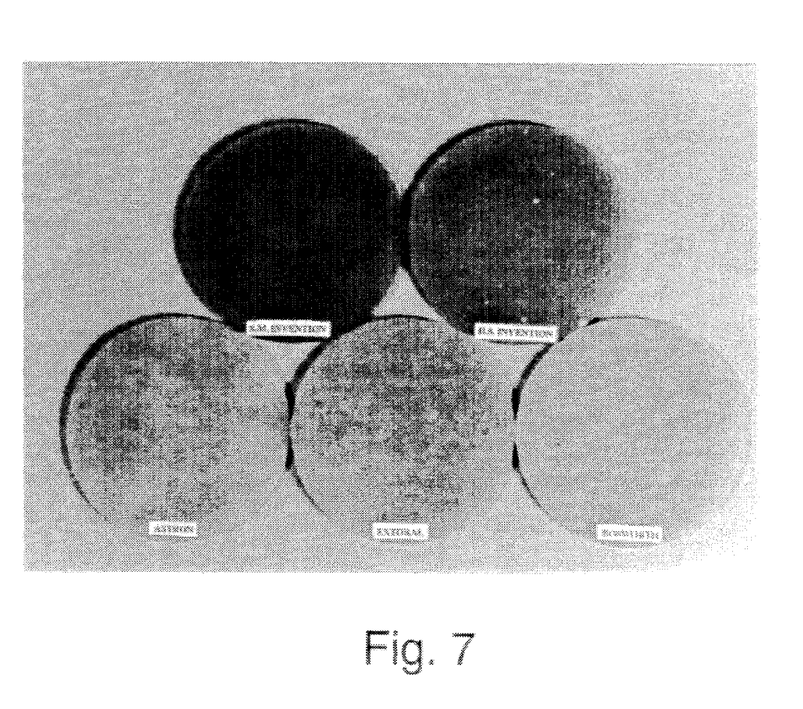
FIG. 7 is a photograph (0.85 times actual size) of: the static mixed denture reline product of the invention made as described in Example 9 (upper left); of the hand spatulated denture reline product of the invention made as described in Example 7 (upper right); of a prior denture reline product sold by Astron (lower left); of a prior denture reline product sold by Extoral (lower middle) and of a prior denture reline product sold by Bosworth (lower right).

Air entrapment during hand spatulation results in porosity of the product formed. Air is not entrapped in a product formed by static mixing, see FIG. 5. Increased porosity is visually shown in FIGS. 2, 3, 4 and 6. FIGS. 2–6 are photographically enlarged portions of the discs of denture reline products showing their grain structures in FIG. 7. Entrapped air is visually apparent in FIGS. 2, 3, 4 and 6. Increased porosity is shown by percent difference in specific gravity between hand mixing and static mixing. The percent difference in specific gravity was greater when static mixing of the composition is used than when hand spatulation of the composition is used. The comparison for percent difference in specific gravity is shown in Table 5:

TABLE 5

SPECIFIC GRAVITY CHANGE

| Composition equal volumes of pastes of Examples | Dihydroxy-p toluidine | Static Mix (Specific Gravity) | Hand Spatulation Mix (Specific Gravity | Percent Difference in Specific Gravity |
|---|---|---|---|---|
| 4 and 5 | 0.125 | 1.188 | 1.178 | 0.85 |

Shelf Life

The shelf life is determined using the Arrhenius equation at 23° C., 37° C., 43° C., 50° C. and 60° C. for compositions stored in two polypropylene cylinders having a piston closing one end. Shelf life is determined by cooling the composition to 23° C. The piston is removed from both cylinders. A pointed probe (50 mm by 1 mm diameter) is inserted into the composition to check for thickening (gellation) at regular time intervals. Shelf life (at each temperature) is the time from initial formulation to just before gellation is first detected in both of the cylinders. The shelf life for example at 23° C. is determined by an Arrhenius plot of the log of the shelf life at each temperature versus the inverse of absolute temperature extended to 23° C. as shown in Fagain et al. Shelf life shows a significant decrease in the package at the higher dihydroxy-p-toluidine level as shown in Tables 6 and 7.

TABLE 6

SHELF LIFE

| Composition equal volumes of pastes of Example | Dihydroxy-p toluidine (Percent by weight) | Shelf life at 60° C. | Shelf life at 23° C. |
|---|---|---|---|
| 4 and 5 | 0.125 | >8 hours | >1200 Days |
| 4 and 6 | 0.250 | 5.5 hours | 850 Days |

This static mixing method allows the use of a lower dihydroxy-p-toluidine levels to attain the required setting time than spatulation, thus resulting in improved color stability, shelf life and porosity.

TABLE 7

DENTURE RELINE

| Example | 7 | 8 | 9 | 10 | 1 (Astron) | 2 (Extoral) | 3 (Bosworth) |
|---|---|---|---|---|---|---|---|
| Composition (Percent by Weight) | | | | | (See Smith et al) | | |
| Benzoyl Peroxide | 0.5 | 0.5 | 0.5 | 0.5 | | | |
| 7,7,9-Trimethyl-4,13-dioxo-3,14-dioxa-5,12-diazahexadecane-1,16-dioldimethacrylate (UDMA) | 60.12 | 60.12 | 60.12 | 60.12 | | | |
| 3-Methacryloxypropyl-trimethoxysilane | 0.01 | 0.01 | 0.01 | 0.01 | | | |
| butylated hydroxytoluene | 0.03 | 0.03 | 0.03 | 0.03 | | | |
| Poly(methyl methacrylate-co-ethylene dimethacrylate-co-ethyl methacrylate-co-styrene) (49.2:0.8:34.0:16.0) (cured bead polymer) | 35.44 | 35.4 | 35.44 | 35.4 | | | |
| Silicon dioxide | 3.6 | 3.6 | 3.6 | 3.6 | | | |
| pigment | 0.01 | 0.01 | 0.01 | 0.01 | | | |
| Camphorquinone | 0.09 | 0.09 | 0.09 | 0.09 | | | |
| (2-hydroxy-4-methoxyphenyl) Benzophenone | 0.15 | 0.15 | 0.15 | 0.15 | | | |
| Dihydroxyethyl-p-toluidine | 0.125 | 0.250 | 0.125 | 0.250 | | | |
| Mixing method | Static | Static | Hand | Hand | Hand | Hand | Hand |
| Starting Consistency | Paste/Paste | Paste/Paste | Paste/Paste | Paste/Paste | Powder/Liquid | Powder/liquid | Powder/liquid |
| Product Characteristics | | | | | | | |
| Work Time (minutes) | 3.25 | 1.00 | 6.35 | 1.75 | 9.5 | | |
| Set Time (minutes) | 4.25 | 1.75 | 7.25 | 2.25 | N/A | | |
| Flexural Strength (MPa) | 93 | | | | 51 | 22 | |
| Flexural Modulus (MPa) | 2720 | | | | 1560 | 1280 | |
| Impact Strength (J/m) | 106 | | | | 35 | 22 | |
| Color Stability (total color change ΔE) | 0.7 | 2 | 1.3 | 2.3 | | | |
| Shelf Life at 23° C. (Days) | 1200 | 850 | | | | | |
| Specific gravity | 1.188 | | 1.178 | | | | |
| Visually perceptible air entrapment | no | no | yes | yes | yes | yes | yes |

The properties of the polymerizing and cured composition, working time and setting times, color stability and shelf life at 23° C., are as shown in combined table. Polymerization proceeds more rapidly after passing through a static mixer than after mixing with hand spatulation on a mixing pad.

It should be understood that while the present invention has been described in considerable detail with respect to certain specific embodiments thereof, it should not be considered limited to such embodiments but may be used in other ways without departure from the spirit of the invention and the scope of the appended claims.

We claim:

1. A method of forming a denture reline to improve the fit of a denture to the soft tissue contours of the mouth of a patient, comprising:

providing a first polymerizable paste composition comprising a free radical generating peroxide oxidizing agent of a catalyst system, a stabilizer effective to prevent polymerization for at least 180 days at 23° C. prior to mixing and at least one polymerizable acrylic compound, and a second polymerizable paste composition comprising a reducing agent for said peroxide and at least one polymerizable acrylic compound, mixing said polymerizable paste compositions in a static mixer to form a polymerizing paste composition, applying said polymerizing paste composition to a denture, and shaping the polymerizing paste composition to areas of soft tissue of the mouth of the patient said polymerizing paste composition substantially self curing in the patient's mouth within less than about 5 minutes.

2. The method of claim 1 wherein said second polymerizable paste composition further comprises a photoinitiator.

3. The method of claim 2 wherein said photoinitiator comprises camphorquinone.

4. The method of claim 1 wherein said applying comprises extruding said polymerizing paste composition onto said denture.

5. The method of claim 1 wherein said reducing agent is dihydroxyethyl-p-toluidine.

6. The method of claim 1 wherein said static mixer is connected in fluid flow communication with each said polymerizable paste composition and each said polymerizable paste composition is substantially free of solvent.

7. The method of claim 1 wherein each said container has an oxygen permeability coefficient of at least about $0.4 \times 10^{-10}$ cm$^2$/sec (cm Hg).

8. The method of claim 1 wherein each said polymerizable paste composition in each said container has a shelf life of at least one year at 23° C.

9. The method of claim 1 wherein said catalyst system comprises benzoyl peroxide, benzopinacole or tertiary butyl perisononanoate.

10. The method of claim 1 wherein each said polymerizing composition is moldable for about 3 minutes before hardening to form said dental product.

11. The method of claim 1 further comprising curing said denture reline in a heat curing oven.

12. The method of claim 1 further comprising curing said denture reline in a light curing oven.

13. The method of claim 1 wherein said dental product has a specific gravity at least 0.5% greater than a corresponding product formed by hand spatulation of said polymerizable paste compositions, and forming and curing the spatulated paste composition.

14. A method of forming a denture reline to improve the fit of a denture to the soft tissue contours of the mouth of a patient comprising: providing a first polymerizable paste composition comprising a free radical generating peroxide oxidizing agent of a free radical generating catalyst system, a stabilizer effective to prevent polymerization for at least 180 days at 23° C. prior to mixing and at least one polymerizable acrylic compound, and a second polymerizable paste composition comprising a reducing agent for said peroxide and at least one polymerizable acrylic compound, mixing said polymerizable paste compositions in a static mixer to form a polymerizing paste composition having a redox catalyst system for the polymerization of said acrylic compound, molding said polymerizing paste composition to areas of soft tissue of the mouth of the patient to form a denture reline.

15. A method of making a denture reline to improve the fit of a denture to the soft tissue contours of the mouth of a patient comprising: providing a first polymerizable paste composition comprising a free radical generating peroxide oxidizing agent of a free radical generating catalyst system, a stabilizer effective to prevent polymerization for at least 180 days at 23° C. prior to mixing and at least one polymerizable acrylic compound, and a second polymerizable paste composition comprising a reducing agent for said peroxide and at least one polymerizable acrylic compound, extruding said paste compositions through a static mixer to form a polymerizing paste, molding said polymerizing paste to areas of soft tissue in the patient's mouth and then light curing said polymerizing paste to form a denture reline.

16. The method of claim 15 further comprising removing said denture from said mold and then irradiating said denture with light in a light curing apparatus.

17. The method of claim 1, 14 or 15 further comprising placing said polymerizing paste in a light curing oven.

18. A denture reline product made by a process to improve the fit of a denture to the soft tissue contours of the mouth of a patient comprising: providing a first polymerizable paste composition comprising a free radical generating peroxide oxidizing agent of a free radical generating catalyst system, a stabilizer effective to prevent polymerization for at least 180 days at 23° C. prior to mixing and at least one polymerizable acrylic compound, and a second polymerizable paste composition comprising a reducing agent for said peroxide and at least one polymerizable acrylic compound, pressing said paste compositions from at least two containers through a static mixer onto a denture to form a polymerizing paste without inclusion of air by entrapment, impressing said polymerizing paste to soft tissue in a patient's mouth to form a denture reline.

19. The product of claim 18 wherein said polymerizing paste is substantially porosity free.

20. A denture reline product made by a process to improve the fit of a denture to the soft tissue contours of the mouth of a patient and comprising: providing a first polymerizable paste composition comprising a free radical generating peroxide oxidizing agent of a free radical generating catalyst system, a stabilizer effective to prevent polymerization for at least 180 days at 23° C. prior to mixing and at least one polymerizable acrylic compound, and a second polymerizable paste composition comprising a reducing agent for said peroxide and at least one polymerizable acrylic compound, extruding said paste compositions from at least two containers through a static mixer to form a polymerizing paste, molding said polymerizing paste to soft tissue in the patient's mouth to form a denture reline.

21. The product of claim 20 wherein said polymerizing paste is substantially porosity free.

* * * * *